United States Patent [19]

Freund et al.

[11] Patent Number: 4,941,911
[45] Date of Patent: Jul. 17, 1990

[54] 2-PHENYLPYRIDAZIN-3-ONE COMPOUNDS, THEIR PREPARATION AND THEIR USE AS HERBICIDES

[75] Inventors: Wolfgang Freund, Neustadt; Gerhard Hamprecht, Weinheim; Bruno Wuerzer, Otterstadt; Karl-Otto Westphalen, Speyer; Norbert Meyer, Ladenburg, all of Fed. Rep. of Germany

[73] Assignee: BASF Aktiengesellschaft, Ludwigshafen, Fed. Rep. of Germany

[21] Appl. No.: 321,064

[22] Filed: Mar. 9, 1989

[51] Int. Cl.$^5$ .................... A01N 43/58; C07D 237/14
[52] U.S. Cl. .................................... 71/92; 71/90; 544/238; 544/240
[58] Field of Search ................ 544/238, 240; 514/247; 71/92

[56] References Cited

U.S. PATENT DOCUMENTS

| | | | |
|---|---|---|---|
| 3,849,107 | 11/1974 | Fischer et al. | 71/92 |
| 4,132,541 | 1/1979 | Hashimoto | 71/127 |
| 4,366,189 | 12/1980 | Burdeska et al. | . |
| 4,523,946 | 6/1985 | Parg et al. | 544/239 |
| 4,576,630 | 3/1986 | Parg et al. | 544/240 |
| 4,844,729 | 7/1989 | Becker et al. | 71/92 |

FOREIGN PATENT DOCUMENTS 1439067  4/1966  France ................ 544/240

0273975 11/1987 Japan .................. 544/238

*Primary Examiner*—Donald G. Daus
*Attorney, Agent, or Firm*—Keil & Weinkauf

[57] ABSTRACT

2-Phenylpyridazin-3-one compounds of the formulae

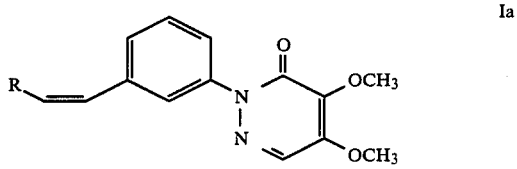

Ia

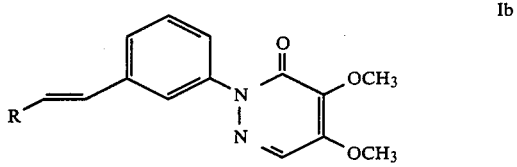

Ib where R is $C_1$–$C_8$-alkyl; substituted or unsubstituted benzyl; substituted or unsubstituted $C_3$–$C_8$-cycloalkyl; a 4- to 6-membered heteroaliphatic ring containing an oxygen or a sulfur atom or an N—$CH_3$ group as ring member; substituted or unsubstituted styryl; a substituted or unsubstituted 5- or 6-membered aromatic or heteroaromatic ring which may be benzofused, processes for their manufacture, and their use.

9 Claims, No Drawings

2-PHENYLPYRIDAZIN-3-ONE COMPOUNDS, THEIR PREPARATION AND THEIR USE AS HERBICIDES

The present invention relates to 2-phenyl-pyridazin-3-one compounds of the formulae Ia and Ib

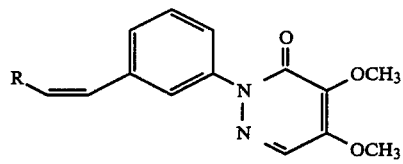

Ia

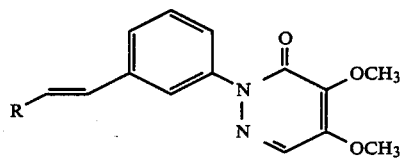

Ib where R is $C_1$–$C_8$-alkyl; benzyl, where the aromatic ring may carry 1 to 3 of the substituents halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio and/or cyano; $C_3$–$C_8$-cycloalkyl which may carry 1 to 3 of the substituents $C_1$–$C_4$-alkyl, $C_1$–$C_4$-haloalkyl, $C_1$–$C_4$-alkoxy and/or $C_1$–$C_4$-haloalkoxy; a 4-membered to 6-membered heteroaliphatic ring containing an oxygen or sulfur atom or an N—$CH_3$ group as a ring member; styryl, where the aromatic ring may carry 1 to 3 of the substituents nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio and/or cyano; a 5-membered or 6-membered aromatic ring which may contain one or two nitrogen, oxygen and/or sulfur atoms as ring members and where this ring may furthermore be benzofused and may carry 1 to 4 of the substituents $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, halogen, nitro, cyano, amino, di-$C_1$–$C_4$-alkylamino, $C_2$–$C_6$-acylamino, $C_1$–$C_4$-alkoxycarbonyl, phenoxy, phenylthio and/or a bridge

which is bonded to the ortho position of the aromatic ring, X is oxygen or sulfur and n is 1 and m is simultaneously 1 or 2 or n is 0 or m is simultaneously 3, 4 or 5, in particular compounds Ia and Ib in which R is a 6-membered aromatic ring which may furthermore be benzofused and may carry 1 to 4 of the substituents $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, halogen, nitro, cyano, amino, di-$C_1$–$C_4$-alkylamino, $C_2$–$C_6$-acylamino, $C_1$–$C_4$-alkoxycarbonyl, phenoxy, phenylthio and/or a bridge

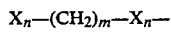

which is bonded to the ortho position of the aromatic ring, X is oxygen or sulfur and n is 1 and m is simultaneously 1 or 2 or n is 0 and m is simultaneously 3, 4 or 5.

The present invention furthermore relates to processes for the preparation of the compounds Ia and Ib and their use in herbicides for controlling undesirable plant growth.

German Laid-Open Application DOS 3,617,997 discloses compounds having the general structure

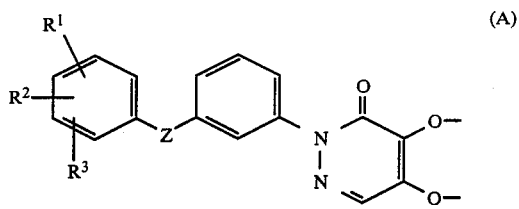

(A)

where Z is the link by means of a $C_1$–$C_5$-alkylene chain.

It is an object of the present invention to provide compounds which are superior to the known herbicides in their biological properties with regard to their action against undesirable plants, without damaging the crops.

We have found that this object is achieved and that the novel compounds of the formulae Ia and Ib defined at the outset are more effective against weeds or have improved selectivity with respect to important crop plants.

We have also found processes for the preparation of the compounds Ia and Ib.

The novel compounds of the formulae Ia and Ib are obtained by the following processes:

(A) By a conventional Wittig reaction of a phosphonium salt of the formula II and an aldehdye of the formula III, where R has the meanings stated for formula I, compounds of the formula I being obtained (cf. Houben-Weyl, Vol. 5/1b, page 383).

III

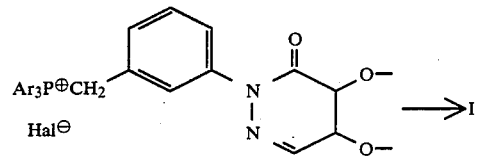

II

The process is advantageously carried out by reacting the starting material of the formula II with an aldehyde of the formula III in an organic solvent in the presence of a base for from 0.5 to 24 hours at from 0° C. to the boiling point of the solvent chosen. The starting materials of the formulae II and III are advantageously used in roughly stoichiometric amounts. Particularly preferred solvents are alcohols, eg. methanol or ethanol, or amides, such as dimethylformamide, and, for example, alkali metal alcoholates may be used as the bases. The compounds of the formula II preferably contain aryl radicals, particularly preferably unsubstituted or substituted phenyl radicals, and, as halogen anions, in particular chloride or bromide, owing to the good availability. The reaction is generally complete after 4–8 hours and working up can be carried out in a conventional manner. If the end product is obtained in solid form, it is isolated, for example, by filtering off the precipitate under suction. If, on the other hand, the end product is in solution in the solvent, the latter is distilled off under reduced pressure. The residue is partitioned between water and an organic solvent, and the end product is obtained by evaporation. Purification can be carried out, for example, by recrystallization or chromatography.

(B) Compounds of the formula I are also obtained by a Horner-Emmons reaction of a phosphonate of the formula IV with an aldehyde of the formula III (cf. Houben-Weyl, Vol. 12/1, page 523, and Vol. 5/1b, page 395).

R—CHO +

III

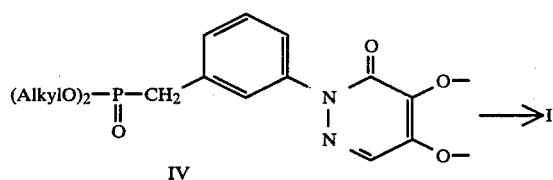

IV

The process is advantageously carried out by reacting the phosphonate, for example the methyl or ethyl com-pound IV, with the aldehyde III in an organic solvent in the presence of a base at from −20° C. to the boiling point of the solvent used. The starting materials are used in roughly stoichiometric amounts. The solvents used may be conventional organic ones: ethers, such as diethyl ether or tetrahydrofuran, amides, eg. dimethylformamide, or aromatic hydrocarbons, eg. benzene or toluene; preferred bases are alkali metal hydrides. The reaction is generally complete after 4–8 hours and at most 24 hours. Working up is carried out in a conventional manner. If the end product is obtained in solid form, it is isolated, for example, by filtering off the precipitate under suction. If, on the other hand, the end product is in solution in the solvent, the solution is partitioned between water and an organic solvent and the reaction product of the formula I is obtained by evaporating down the organic solvent. The product of the formula I can be purified, for example, by recrystallization or chromatography.

Phosphonium compounds II and phosphonates IV can be prepared in a conventional manner from a corresponding halide and a triarylphosphine or a trialkyl phosphite (cf. Houben-Weyl, Vol. 12/1, page 79 and page 433, respectively):

The halide VI is in turn obtained from the known methyl compound (V; cf. FR-A-2 099 642) by halogenation (cf. Houben-Weyl, Vol. 5/4, page 331; Vol. 5/3, page 503, 800; Vol. 4/5a, page 134).

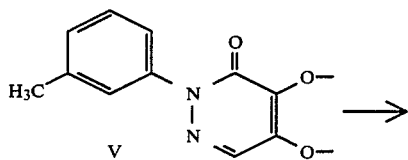

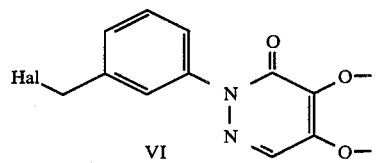

Preferred halogens in the compounds of the formula VI are chlorine and bromine. Halogenation can be effected either with elemental halogen, preferably with simultaneous exposure to light, or with halogen carriers in the presence of free radical initiators, such as dibenzoyl peroxide or 2,2′-azobisisobutyronitrile, or with exposure to light. Particularly suitable halogen carriers are N-halogen compounds, for example N-bromosuccinimide or N-chlorosuccinimide.

The novel compounds I are as a rule crystalline or viscous compounds. In the stated processes, they are formed, as a rule, as cis/trans mixtures of Ia and Ib, and in general predominantly the trans compound Ib can be obtained by process (B). The mixtures of Ia and Ib can generally be separated into the pure compounds Ia and Ib by recrystallization and chromatography.

For the 2-phenylpyridazin-3-one compounds Ia and Ib to be used in accordance with regulations, suitable substituents R are the following radicals: alkyl such as methyl, ethyl, propyl, 1-methylethyl, butyl, 1-methylpropyl, 2-methylpropyl, 1,1-dimethylpropyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 1-propylbutyl or octyl, in particular 1,1-dimethylethyl, 2,2-dimethylpropyl or 1,2-dimethylbutyl; heteroaliphatic rings, such as oxethanyl, thiethanyl, N-methylazetidinyl, oxolanyl, thiolanyl, N-methylazolidinyl, dioxolanyl, thioxolanyl, dithiolanyl, N-methyloxazolidinyl, N-methylthiazolidinyl, tetrahydropyranyl, tetrahydrothiopyranyl, N-methylpiperidyl, tetrahydro-1,3-dioxanyl, tetrahydro-1,4-dioxanyl, tetrahydro-1,3-thioxanyl, tetrahydro-1,4-thioxanyl, tetrahydro-1,3-dithianyl, N-methylmorpholinyl, N-methylhexahydro-1,3-oxazinyl, N-methylhexahydro-1,3-thiazinyl or N-methylhexahydro-1,4-thiazinyl; benzyl, phenyl, naphthyl, styryl or one of the following heteroaromatic groups: 2-, 3- or 4-pyridyl, 2-, 4- or 5-pyrimidyl, 2- or 3-pyrazinyl, 2-, 3- or 4-quinolyl, 2- or 3-thienyl, 2- or 3-furyl, 2- or 3-pyrrolyl, 2-, 4- or 5-thiazolyl, 2-, 4- or 5-imidazolyl, 2-, 4- or 5-oxazolyl, 3-, 4- or 5-isothiazolyl, 3-, 4- or 5-pyrazolyl, 3-, 4- or 5-isoxazolyl, 2-thiadiazolyl, 2-oxadiazolyl, 2-benzothiazolyl, 2-benzoxazolyl or 2-benzimidazolyl.

These aromatic rings may each be unsubstituted or monosubstituted to trisubstituted. Suitable substituents are the following groups: cyano; halogen, such as fluorine, chlorine, bromine or iodine, in particular fluorine, chlorine or bromine; $C_1$–$C_4$-alkyl as stated above, in particular methyl, ethyl and 1-methylethyl; haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl, in particular difluoromethyl, trifluoromethyl, 2,2,2-trifluoroethyl and pentafluoroethyl; alkoxy, such as methoxy, ethoxy, propoxy, 1-methylethoxy, butoxyl, 1-methylpropoxy, 2-methylpropoxy and 1,1-dimethylethoxy, in particular methoxy, ethoxy, 1-methylethoxy and 1,1-dimethylethoxy; haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, in particular trifluoromethoxy; alkylthio, such as methylthio, ethylthio, propylthio, 1-methylethylthio, butylthio, 1-methylpropylthio, 2-methylpropylthio and 1,1-dimethylethylthio, in particular methylthio and ethylthio; haloalkylthio, such as difluoromethylthio, trifluoromethylthio, chlorodifluoromethylthio, dichlorofluoromethylthio, 1-fluoroethylthio, 2-fluoroethylthio, 2,2-difluoroethylthio, 1,1,2,2-tetrafluoroethylthio, 2,2,2-trifluoroethylthio, 2-chloro-1,1,2-trifluoroethylthio and pentafluoroethylthio, in particular trifluoroethylthio.

This styryl radical can, in addition to the abovementioned groups, also be substituted by nitro groups, while the 5-membered or 6-membered aromatic and heteroaromatic radicals may furthermore carry the following substituents: phenoxy, phenylthio, amino, which may be disubstituted by the abovementioned $C_1$–$C_4$-alkyl groups or monosubstituted or disubstituted by acyl groups, such as acetyl, propionyl, isopropionyl, butyryl, 2-methylpropionyl, pentanoyl, 2-methylbutyryl, 3-methylbutyryl, 2,2-dimethylpropionyl, hexanoyl, 2-methylpentanoyl, 3-methylpentanoyl, 4-methylpentanoyl, 2,2-dimethylbutyryl, 2,3-dimethylbutyryl, 3,3-dimethylbutyryl and 2-ethylbutyryl, in particular acetyl and propionyl; and alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl and 1,1-dimethylethoxycarbonyl, in particular ethoxycarbonyl and ethoxycarbonyl.

In addition, adjacent ring positions of these aromatic rings may be linked by a bridge —$X_n$—$(CH_2)_m$—$X_n$—, where X is oxygen or sulfur and n is 1 when m is 1 or 2 and n is 0 when m is 3, 4 or 5. Examples of such bridges are listed below:
—O—CH$_2$—O—, —O—CH$_2$CH$_2$—O—, —S—CH$_2$—S—, —S—CH$_2$CH$_2$—S—, —CH$_2$CH$_2$CH$_2$—, —CH$_2$CH$_2$CH$_2$CH$_2$— and —CH$_2$CH$_2$CH$_2$CH$_2$CH$_2$—.

The 2-phenylpyridazin-3-one compounds Ia and Ib, or the herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 19 is mixed with 10 parts by weight of N-methyl-alpha-pyrrolidone. A mixture is obtained which is suitable for application in the form of very fine drops.

II. 20 parts by weight of compound no. 47a is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 75 is dissolved in a mixutre consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 104 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 137 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 155 is intimately mixed with 97 parts by weight of particulate kaolin. A dust is obtained containing 3% by weight of the active ingredient.

VII. 30 parts by weight of compound no. 166 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 164 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 5.0, preferably 0.01 to 0.5, kg of active ingredient per hectare. In view of the number of application methods possible, the compounds according to the invention, or agents containing them, may be used in a further large number of crops for removing unwanted plants. The following crops are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liverica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium aboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |

-continued

| Botanical name | Common name |
| --- | --- |
| Triticum durum | durum wheat |
| Vaccinium corymbosum | blueberries |
| Vaccinium vitis-idaea | cranberries |
| Vicia faba | tick beans |
| Vigna sinensis (V. unguiculate) | cow peas |
| Vitis vinifera | grapes |
| Zea mays | Indian corn, sweet corn, maize |

To increase the spectrum of action and to achieve synergistic effects, the compounds of the formulae Ia and Ib may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, phenyloxy- or heteroaryloxy-phenylpropionic acids and salts, esters and amides thereof, etc.

It may also be useful to apply the novel compounds of the formula Ia and Ib, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

The directions given in the synthesis examples below were employed, after appropriate modifications to the starting materials, to obtain further compounds of the formulae Ia and Ib; the compounds obtained are listed in the tables below with physical data. Those compounds for which no data are given may be produced analogously from the appropriate materials. In view of their close structural similarity with the compounds produced and investigated, they are expected to have a similar action.

EXAMPLE 1

Manufacturing route via the Wittig compound (A) While stirring vigorously and exposing to light from a 300 watt incandescent lamp, a solution of 80.0 g of bromine in 400 ml of dichloromethane is dripped into a solution of 105 g of 1-(3'-methylphenyl)-4,5-dimethoxypyridazin-6-one and 51.6 g of sodium acetate in 1.5 liters of dichloromethane and 500 ml of water. The dichloromethane is then separated off and the remainder is washed with a sodium carbonate solution and concentrated. There is obtained 124 g of 1-(3'-bromomethylphenyl)-4,5-dimethoxypyridazin-6-one of m.p. 67°–69° C. and a purity of 90%.

(B) A solution of 120 g of 1-(3'-bromomethylphenyl)-4,5-dimethoxypyridazin-6-one (85% pure) and 97.0 g of triphenylphosphine in 500 ml of acetone is refluxed for 2.5 hours. Suction filtration gives 167 g of 3-(4',5'-dimethoxypyridazin-6'-one)-phenylmethyltriphenylphosphonium bromide of m.p. 217° C. (decomp.).

(C) A suspension of 15.0 g o 1-(3'-methylphenyl)-4,5-dimethoxypyridazin-6-one, 12.2 g of N-chlorosuccinimide and 2.3 g o dibenzoyl peroxide in 150 ml of chlorobenzene is stirred for 3 hours at the boiling temperature, concentrated, taken up in toluene and chromatographed using silica gel. There is obtained 5.6 g of brown crystals which consist, according to $^1$H—NMR, of starting material (50%), 1-(3'-chloromethylphenyl)-4,5-dimethoxypyridazin-6-one (35%) and 1-(3'-dichloromethylphenyl)-4,5-dimethoxypyridazin-6-one (15%), and which are separated and purified.

(D) 9.56 g of 1-(3'-chloromethylphenyl)-4,5-dimethoxypyridazin-6-one (88% pure) and 7.85 g of triphenylphosphine ae heated in 100 ml of toluene for 8 hours at 80° C. and for 5 hours at boiling temperature, the mixture is concentrated and the residue is triturated with acetone. There is obtained 9 g of 3-(4',5'-dimethoxypyridazin-6'-one)-phenylmethyltriphenylphosphonium chloride of m.p. 198°–201° C.

(E) 7.20 g of 30% strength sodium methylate in methanol is dripped into a suspension of 23.5 g of 3-(4',5'-dimethoxypyridazin-6'-one)-phenylmethyltriphenylphosphonium bromide in 100 ml of methanol, and the mixture is stirred for 20 minutes at room temperature. Subsequently, 4.20 g of benzaldehyde is dripped in, and the mixture is stirred for 6 hours at room temperature, diluted with water and extracted by shaking with ethyl acetate. The oil remaining after concentration is chromatographed on silica gel (cyclohexane/ethyl acetate). There is obtained 10.6 g of cis- and trans-3-(4',5'-dimethoxypyridazin-6'-one)-stilbene as a colorless oil.

The cis/trans isomers can be separated by repeat chromatography (cyclohexane/ethyl acetate). There is obtained as a more readily elutable substance cis-3-(4',5'-dimethoxypyridazin-6'-one)-stilbene of m.p. 48°–51° C. (compound no. 1).

The second fraction is trans-3-(4',5'-dimethoxypyridazin-6'-one)-stilbene of m.p. 87°–91° C. (compound no. 2).

MANUFACTURING ROUTE VIA THE PHOSPHONATE (A) A suspension of 152 g of 1-(3'-methylphenyl)-4,5-dimethoxypyridazin-6-one, 165 g of N-bromosuccinimide and 10 g of 2,2'-azoisobutyric dinitrile in 1 liter of 1,1,1-trichloroethane is refluxed for 5 hours. The mixture is cooled and subjected to suction filtration, and the filtrate is concentrated. There is obtained 252 g of brown crystals of m.p. 53°–58° C., which, according to $^1$H—NMR, consist to the extent of 73% of 1-(3-bromomethylphenyl)-4,5-dimethoxypyridazin-6-one.

(B) 40 g of 1-(3'-bromomethylphenyl)-4,5-dimethoxypyridazin-6-one (50% pure, according to $^1$H—NMR) and 66 g of phosphorous acid triethyl ester are heated to 120° C. After 1 hour, the excess of phosphorous acid triethyl ester is removed under reduced pressure and the residue is chromatographed on silica gel (ethyl acetate/ethanol=90/10). There is obtained 20.2 g of diethyl 3-(4',5'-dimethoxypyridazin-6'-one)-phenylmethylphosphonate as a yellow oil, which crystallizes after trituration with ether/pentane. The melting point of the colorless crystals is 71°–72° C.

(C) 10.6 g of the phosphonate from B in 50 ml of absolute tetrahydrofuran is dripped into 1.15 g of sodium hydride. After 30 minutes, a solution of 3.18 g of benzaldehyde in 50 ml of absolute tetrahydrofuran is dripped in at room temperature. The mixture is stirred overnight, poured into water, and extracted by shaking with diethyl ether. Concentration gives 8.8 g of trans-3-(4',5'-dimethoxypyridazin-6'-one)-stilbene of m.p. 89.90° C.

EXAMPLE 2

At 80° C., 3.40 g of the compound listed as no. 157 in the following table is added to 5.30 g of ethanolamine. The mixture is stirred for 10 minutes at 80° C., and partitioned between water and ethyl acetate. The residue remaining after concentration of the ethyl acetate is stirred with water and chromatographed on silica gel (toluene/acetone). There is obtained 1-amino-4-(3'-(4",5"-dimethoxypyridazin-6"-one)-stilbene as a colorless oil (compound no. 3); cis/trans mixture (H—NMR): cis: 7.80 (S; 1H); trans: 7.85 (S; 1H).

TABLE 1

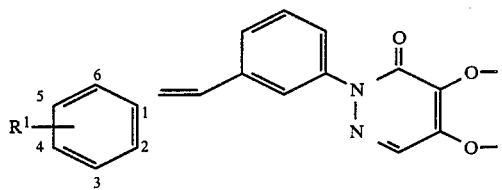

| No. | $R^1$ | mp (°C.) | cis/trans ratio | H-NMR (ppm) |
|---|---|---|---|---|
| 4 | 2-$CH_3$ | | | |
| 5 | 3-$CH_3$ | | | |
| 6 | 4-$CH_3$ | | | |
| 7 | 2-$C_2H_5$ | | | |
| 8 | 3-$C_2H_5$ | | | |
| 9 | 4-$C_2H_5$ | | | |
| 10 | 3-n-$C_3H_7$ | | | |
| 11 | 4-n-$C_3H_7$ | | | |
| 12 | 3-i-$C_3H_7$ | | | |
| 13 | 4-i-$C_3H_7$ | | | |
| 14 | 3-n-$C_4H_9$ | | | |
| 15 | 4-n-$C_4H_9$ | | | |
| 16 | 3-sec-$C_4H_9$ | | | |
| 17 | 4-sec-$C_4H_9$ | | | |
| 18 | 3-t-$C_4H_9$ | | | |
| 19 | 4-t-$C_4H_9$ | oil | cis | 7.79 (s; 1H) |
| 20 | 4-t-$C_4H_9$ | 132–140 | trans | |
| 21 | 3-n-$C_5H_{11}$ | | | |
| 22 | 4-n-$C_5H_{11}$ | | | |
| 23 | 3-n-$C_6H_{13}$ | | | |
| 24 | 4-n-$C_6H_{13}$ | | | |
| 25 | 3-phenyl | | | |
| 26 | 4-phenyl | | | |
| 27 | 2,3-$(CH_3)_2$ | | | |
| 28 | 2,4-$(CH_3)_2$ | | | |
| 29 | 2,5-$(CH_3)_2$ | | | |
| 30 | 2,6-$(CH_3)_2$ | | | |
| 31 | 3,4-$(CH_3)_2$ | | | |
| 32 | 3,5-$(CH_3)_2$ | | | |
| 33 | 2,3,4-$(CH_3)_3$ | | | |
| 34 | 2,3,5-$(CH_3)_3$ | | | |
| 35 | 2,4,5-$(CH_3)_3$ | | | |
| 36 | 2,4,6-$(CH_3)_3$ | | | |
| 37 | 3,4,5-$(CH_3)_3$ | | | |
| 38 | 2-$CF_3$ | oil | cis/trans = 2/1 | cis: 7.77 (s; 1H); trans: 7.84 (s; 1H) |
| 39 | 3-$CF_3$ | oil | cis/trans = 1/1 | cis: 7.79 (s; 1H); trans: 7.86 (s; 1H) |
| 40 | 4-$CF_3$ | 61 | cis | |
| 41 | 4-$CF_3$ | 88–94 | trans | |
| 42 | 2-F | 75–80 | cis/trans = 2/1 | |
| 43 | 3-F | oil | cis | 7.79 (s; 1H) |
| 44 | 3-F | 105–110 | cis/trans = 1/3 | |
| 45 | 4-F | oil | cis | 7.81 (s; 1H) |
| 46 | 4-F | 107–112 | trans | |
| 47 | 2-Cl | oil | cis/trans = 1/1 | cis: 7.77 (s; 1H); trans: 7.84 (s; 1H) |
| 47a | 2-Cl | oil | cis | 7.77 (s; 1H) |
| 48 | 3-Cl | oil | cis | 7.78 (s; 1H) |
| 49 | 3-Cl | 119–126 | trans | |
| 50 | 4-Cl | 50–53 | cis | |
| 51 | 4-Cl | 114–118 | trans | |
| 52 | 2-Br | | | |
| 53 | 3-Br | | | |
| 54 | 4-Br | 119–123 | cis/trans = 1/1 | |
| 55 | 2,3-$F_2$ | | | |
| 56 | 2,4-$F_2$ | | | |
| 57 | 2,5-$F_2$ | | | |
| 58 | 2,6-$F_2$ | | | |
| 59 | 2,3-$Cl_2$ | | | |
| 60 | 2,4-$Cl_2$ | oil | cis/trans = 1/2 | cis: 7.78 (s; 1H); trans: 7.82 (s; 1H) |
| 60a | 2,4-$Cl_2$ | 108–110 | cis | |
| 61 | 2,5-$Cl_2$ | | | |
| 62 | 2,6-$Cl_2$ | | | |
| 63 | 3,4-$Cl_2$ | | | |
| 64 | 3,5-$Cl_2$ | | | |
| 65 | 2,3,4-$Cl_3$ | | | |
| 66 | 2,3,5-$Cl_3$ | | | |
| 67 | 2,4,6-$Cl_3$ | | | |
| 68 | 3,4,5-$Cl_3$ | | | |
| 69 | 2-CN | | | |
| 70 | 3-CN | | | |
| 71 | 4-CN | 165–168 | trans | |
| 72 | 4-CN | 56–60 | cis | |
| 73 | 2-$OCH_3$ | | | |
| 74 | 3-$OCH_3$ | | | |
| 75 | 4-$OCH_3$ | oil | cis/trans = 2/1 | cis: 7.80 (s; 1H); trans: 7.86 (s; 1H) |
| 76 | 2-$OC_2H_5$ | | | |
| 77 | 3-$OC_2H_5$ | | | |
| 78 | 4-$OC_2H_5$ | | | |
| 79 | 3-O-n-$C_3H_7$ | | | |
| 80 | 4-O-n-$C_3H_7$ | | | |
| 81 | 3-O-i-$C_3H_7$ | | | |
| 82 | 4-O-i-$C_3H_7$ | | | |
| 83 | 3-O-n-$C_4H_9$ | | | |
| 84 | 4-O-n-$C_4H_9$ | | | |
| 85 | 3-O-t-$C_4H_9$ | | | |
| 86 | 4-O-t-$C_4H_9$ | | | |
| 87 | 4-O-n-$C_5H_{11}$ | | | |
| 88 | 4-O-n-$C_6H_{13}$ | | | |
| 89 | 3-$OC_6H_5$ | | | |
| 90 | 4-$OC_6H_5$ | | | |
| 91 | 2,3-$(OCH_3)_2$ | | | |
| 92 | 2,4-$(OCH_3)_2$ | | | |
| 93 | 2,5-$(OCH_3)_2$ | | | |
| 94 | 2,6-$(OCH_3)_2$ | | | |
| 95 | 3,4-$(OCH_3)_2$ | | | |
| 96 | 3,5-$(OCH_3)_2$ | | | |
| 97 | 3,4,5-$(OCH_3)_3$ | | | |
| 98 | 2-$OCF_3$ | | | |
| 99 | 3-$OCF_3$ | | | |
| 100 | 4-$OCF_3$ | | | |
| 101 | 2-$OCF_2CHF_2$ | | | |
| 102 | 3-$OCF_2CHF_2$ | | | |
| 103 | 4-$OCF_2CHF_2$ | oil | cis | 7.78 (s; 1H) |
| 104 | 4-$OCF_2CHF_2$ | 91–101 | trans | |
| 105 | 2-O-benzyl | | | |
| 106 | 3-O-benzyl | | | |
| 107 | 4-O-benzyl | | | |
| 108 | 3,4-$OCH_2O$ | | | |
| 109 | 3,4-$OCH_2CH_2O$ | | | |
| 110 | 3,4-$SCH_2O$ | | | |

TABLE 1-continued

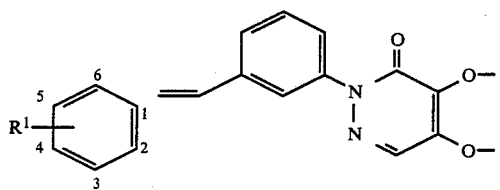

| No. | R¹ | mp (°C.) | cis/trans ratio | H-NMR (ppm) |
|---|---|---|---|---|
| 111 | 3,4-SCH$_2$CH$_2$O | | | |
| 112 | 3,4-SCH$_2$S | | | |
| 113 | 3,4-SCH$_2$CH$_2$S | | | |
| 114 | 2-SCH$_3$ | | | |
| 115 | 3-SCH$_3$ | | | |
| 116 | 4-SCH$_3$ | | | |
| 117 | 2-SC$_2$H$_5$ | | | |
| 118 | 3-SC$_2$H$_5$ | | | |
| 119 | 4-SC$_2$H$_5$ | | | |
| 120 | 3-S-nC$_3$H$_7$ | | | |
| 121 | 4-S-nC$_3$H$_7$ | | | |
| 122 | 3-S-i-C$_3$H$_7$ | | | |
| 123 | 4-S-i-C$_3$H$_7$ | | | |
| 124 | 3-S-n-C$_4$H$_9$ | | | |
| 125 | 4-S-n-C$_4$H$_9$ | | | |
| 126 | 3-S-t-C$_4$H$_9$ | | | |
| 127 | 4-S-t-C$_4$H$_9$ | | | |
| 128 | 4-S-n-C$_5$H$_{11}$ | | | |
| 129 | 4-S-n-C$_6$H$_{13}$ | | | |
| 130 | 2,4-(SCH$_3$)$_2$ | | | |
| 131 | 2,5-(SCH$_3$)$_2$ | | | |
| 132 | 2-SCF$_3$ | | | |
| 133 | 3-SCF$_3$ | | | |
| 134 | 4-SCF$_3$ | | | |
| 135 | 2-NO$_2$ | | | |
| 136 | 3-NO$_2$ | | | |
| 137 | 4-NO$_2$ | 96–105 | cis | |
| 138 | 4-NO$_2$ | 136 | trans | |
| 139 | 2,3-(NO$_2$)$_2$ | | | |
| 140 | 2,4-(NO$_2$)$_2$ | 102–110 | cis | |
| 141 | 2,5-(NO$_2$)$_2$ | | | |
| 142 | 2,6-(NO$_2$)$_2$ | | | |
| 143 | 3,4-(NO$_2$)$_2$ | | | |
| 144 | 3,5-(NO$_2$)$_2$ | | | |
| 145 | 3-NH$_2$ | | | |
| 146 | 2-N(CH$_3$)$_2$ | | | |

TABLE 1-continued

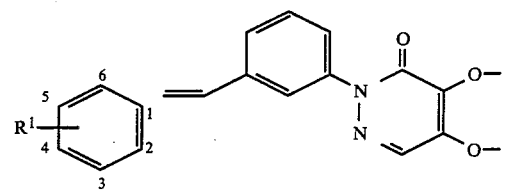

| No. | R¹ | mp (°C.) | cis/trans ratio | H-NMR (ppm) |
|---|---|---|---|---|
| 147 | 3-N(CH$_3$)$_2$ | | | |
| 148 | 4-N(CH$_3$)$_2$ | | | |
| 149 | 2-N(C$_2$H$_5$)$_2$ | | | |
| 150 | 3-N(C$_2$H$_5$)$_2$ | | | |
| 151 | 4-N(C$_2$H$_5$)$_2$ | oil | cis/trans = 1/1 | cis: 7.78 (s; 1H); trans: 7.83 (s; 1H) |
| 152 | 2-NHCOCH$_3$ | | | |
| 153 | 3-NHCOCH$_3$ | | | |
| 154 | 4-NHCOCH$_3$ | | | |
| 155 | 3-phthalimido | 126–131 | cis | |
| 156 | 3-phthalimido | 146–151 | cis/trans = 2/8 | |
| 157 | 4-phthalimido | 104–111 | cis/trans = 2/1 | |
| 158 | 2-NHCOC$_3$H$_7$ | | | |
| 159 | 3-NHCOC$_3$H$_7$ | | | |
| 160 | 4-NHCOC$_3$H$_7$ | | | |
| 161 | 2-COOMe | | | |
| 162 | 3-COOMe | | | |
| 163 | 4-COOMe | | | |

TABLE 1a

| No. | R | mp (°C.) | cis/trans ratio | H-NMR (ppm) |
|---|---|---|---|---|
| 164 | 1-naphthyl | 78–72 | cis/trans = 1/1 | |
| 165 | 2-naphthyl | | | |

TABLE 2a

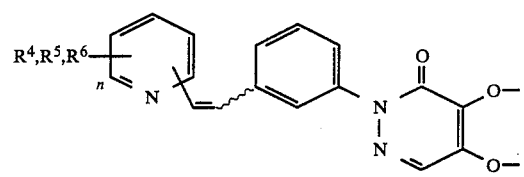

| No. | R⁴, R⁵, R⁶ | Linkage | mp (°C.) | cis/trans ratio | H-NMR (ppm) |
|---|---|---|---|---|---|
| 166 | H | 2 | oil | cis | 7.81(s; 1H) |
| 167 | H | 2 | oil | trans | 7.88(s; 1H) |
| 168 | H | 3 | oil | cis/trans = 1/1 | cis: 7.80(s; 1H); trans: 7.87(s; 1H) |
| 169 | H | 4 | oil | cis/trans = 2/1 | cis: 7.80(s; 1H); trans: 7.89(s; 1H) |
| 170 | 3-CH$_3$ | 2 | | | |
| 171 | 4-CH$_3$ | 2 | | | |
| 172 | 5-CH$_3$ | 2 | | | |
| 173 | 6-CH$_3$ | 2 | | | |
| 174 | 2-CH$_3$ | 3 | | | |
| 175 | 4-CH$_3$ | 3 | | | |
| 176 | 5-CH$_3$ | 3 | | | |
| 177 | 6-CH$_3$ | 3 | | | |
| 178 | 2-CH$_3$ | 4 | | | |
| 179 | 3-CH$_3$ | 4 | | | |
| 180 | 3-F | 2 | | | |
| 181 | 4-F | 2 | | | |

TABLE 2a-continued
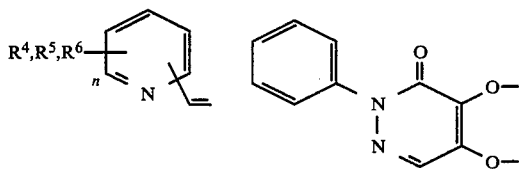
| No. | R⁴, R⁵, R⁶ | Linkage | mp (°C.) | cis/trans ratio | H-NMR (ppm) |
|---|---|---|---|---|---|
| 182 | 5-F | 2 | | | |
| 183 | 6-F | 2 | | | |
| 184 | 3-Cl | 2 | | | |
| 185 | 4-Cl | 2 | | | |
| 186 | 5-Cl | 2 | | | |
| 187 | 6-Cl | 2 | | | |
| 188 | 2-Cl | 3 | | | |
| 189 | 4-Cl | 3 | | | |
| 190 | 5-Cl | 3 | | | |
| 191 | 6-Cl | 3 | | | |
| 192 | 2-Cl | 4 | | | |
| 193 | 3-Cl | 4 | | | |
| 194 | 3-CF$_3$ | 2 | | | |
| 195 | 4-CF$_3$ | 2 | | | |
| 196 | 5-CF$_3$ | 2 | | | |
| 197 | 6-CF$_3$ | 2 | | | |
| 198 | 2-CF$_3$ | 3 | | | |
| 199 | 4-CF$_3$ | 3 | | | |
| 200 | 5-CF$_3$ | 3 | | | |
| 201 | 6-CF$_3$ | 3 | | | |
| 202 | 2-CF$_3$ | 4 | | | |
| 203 | 3-CF$_3$ | 4 | | | |
| 204 | 3-OCH$_3$ | 2 | | | |
| 205 | 4-OCH$_3$ | 2 | | | |
| 206 | 5-OCH$_3$ | 2 | | | |
| 207 | 6-OCH$_3$ | 2 | | | |
| 208 | 2-OCH$_3$ | 3 | | | |
| 209 | 4-OCH$_3$ | 3 | | | |
| 210 | 5-OCH$_3$ | 3 | | | |
| 211 | 6-OCH$_3$ | 3 | | | |
| 212 | 2-OCH$_3$ | 4 | | | |
| 213 | 3-OCH$_3$ | 4 | | | |
| 214 | 3-OCF$_3$ | 2 | | | |
| 215 | 4-OCF$_3$ | 2 | | | |
| 216 | 5-OCF$_3$ | 2 | | | |
| 217 | 6-OCF$_3$ | 2 | | | |
| 218 | 3-SCH$_3$ | 2 | | | |
| 219 | 4-SCH$_3$ | 2 | | | |
| 220 | 5-SCH$_3$ | 2 | | | |
| 221 | 6-SCH$_3$ | 2 | | | |
| 222 | 3-SCF$_3$ | 2 | | | |
| 223 | 4-SCF$_3$ | 2 | | | |
| 224 | 5-SCF$_3$ | 2 | | | |
| 225 | 6-SCF$_3$ | 2 | | | |
| 226 | 3-NO$_2$ | 2 | | | |
| 227 | 4-NO$_2$ | 2 | | | |
| 228 | 5-NO$_2$ | 2 | | | |
| 229 | 6-NO$_2$ | 2 | | | |
| 230 | 3-CN | 2 | | | |
| 231 | 4-CN | 2 | | | |
| 232 | 5-CN | 2 | | | |
| 233 | 6-CN | 2 | | | |
| 234 | 5,6-[—CH=CH—CH=CH—] | 2 | | | |
| 235 | 5,6-[—CH=CH—CH=CH—] | 3 | | | |
| 236 | 5,6-[—CH=CH—CH=CH—] | 4 | | | |
| 237 | 5,6-[—(CH$_2$)$_4$—] | 2 | | | |
| 238 | 5,6-[—(CH$_2$)$_4$—] | 3 | | | |
| 239 | 5,6-[—(CH$_2$)$_4$—] | 4 | | | |

TABLE 2b
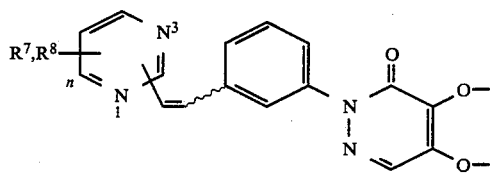
| No. | R⁷, R⁸ | Linkage | mp (°C.) | cis/trans ratio | H-NMR (ppm) |
|---|---|---|---|---|---|
| 240 | H | 2 | | | |
| 241 | H | 4 | | | |
| 242 | H | 5 | | | |
| 243 | 4-CH$_3$ | 2 | | | |
| 244 | 5-CH$_3$ | 2 | | | |
| 245 | 2-CH$_3$ | 4 | | | |
| 246 | 5-CH$_3$ | 4 | | | |
| 247 | 6-CH$_3$ | 4 | | | |
| 248 | 2-CH$_3$ | 5 | | | |
| 249 | 4-CH$_3$ | 5 | | | |
| 250 | 4-Cl | 2 | | | |
| 251 | 5-Cl | 2 | | | |
| 252 | 2-Cl | 4 | | | |
| 253 | 5-Cl | 4 | | | |
| 254 | 6-Cl | 4 | | | |
| 255 | 2-Cl | 5 | | | |
| 256 | 4-Cl | 5 | | | |
| 257 | 4-CF$_3$ | 2 | | | |
| 258 | 5-CF$_3$ | 2 | | | |
| 259 | 2-CF$_3$ | 4 | | | |
| 260 | 5-CF$_3$ | 4 | | | |
| 261 | 6-CF$_3$ | 4 | | | |
| 262 | 2-CF$_3$ | 5 | | | |
| 263 | 4-CF$_3$ | 5 | | | |
| 264 | 4-OCH$_3$ | 2 | | | |
| 265 | 5-OCH$_3$ | 2 | | | |
| 266 | 2-OCH$_3$ | 4 | | | |
| 267 | 5-OCH$_3$ | 4 | | | |
| 268 | 6-OCH$_3$ | 4 | | | |
| 269 | 2-OCH$_3$ | 5 | | | |
| 270 | 4-OCH$_3$ | 5 | | | |
| 271 | 4-SCH$_3$ | 2 | | | |
| 272 | 5-SCH$_3$ | 2 | | | |
| 273 | 2-SCH$_3$ | 4 | | | |
| 274 | 5-SCH$_3$ | 4 | | | |
| 275 | 6-SCH$_3$ | 4 | | | |
| 276 | 2-SCH$_3$ | 5 | | | |
| 277 | 4-SCH$_3$ | 5 | | | |
| 278 | 4-OCF$_3$ | 2 | | | |
| 279 | 5-OCF$_3$ | 2 | | | |
| 280 | 2-OCF$_3$ | 4 | | | |
| 281 | 5-OCF$_3$ | 4 | | | |
| 282 | 6-OCF$_3$ | 4 | | | |
| 283 | 2-OCF$_3$ | 5 | | | |
| 284 | 4-OCF$_3$ | 2 | | | |
| 285 | 4-SCF$_3$ | 2 | | | |
| 286 | 5-SCF$_3$ | 2 | | | |
| 287 | 2-SCF$_3$ | 4 | | | |
| 288 | 5-SCF$_3$ | 4 | | | |
| 289 | 6-SCF$_3$ | 4 | | | |
| 290 | 2-SCF$_3$ | 5 | | | |
| 291 | 4-SCF$_3$ | 5 | | | |
| 292 | 2-NO$_2$ | 5 | | | |
| 293 | 5-NO$_2$ | 4 | | | |
| 294 | 6-NO$_2$ | 4 | | | |
| 295 | 2-CN | 4 | | | |
| 296 | 5-CN | 4 | | | |
| 297 | 6-CN | 4 | | | |
| 298 | 4,5-[—CH=CH—CH=CH—] | 2 | | | |
| 299 | 5,6-[—CH=CH—CH=CH—] | 4 | | | |

TABLE 2c
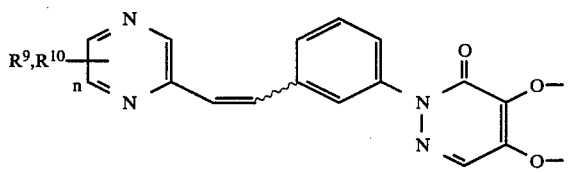
| No. | R⁹, R¹⁰ | mp (°C.) | cis/trans ratio | H-NMR (ppm) |
|---|---|---|---|---|
| 300 | H | | | |
| 301 | 3-CH₃ | | | |
| 302 | 5-CH₃ | | | |
| 303 | 6-CH₃ | | | |
| 304 | 3-F | | | |
| 305 | 5-F | | | |
| 306 | 6-F | | | |
| 307 | 3-Cl | | | |
| 308 | 5-Cl | | | |
| 309 | 6-Cl | | | |
| 310 | 3-OCH₃ | | | |
| 311 | 5-OCH₃ | | | |
| 312 | 6-OCH₃ | | | |
| 313 | 3-CF₃ | | | |
| 314 | 5-CF₃ | | | |
| 315 | 6-CF₃ | | | |
| 316 | 3-OCF₃ | | | |
| 317 | 5-OCF₃ | | | |
| 318 | 6-OCF₃ | | | |
| 319 | 3-SCH₃ | | | |
| 320 | 5-SCH₃ | | | |
| 321 | 6-SCH₃ | | | |
| 322 | 3-SCF₃ | | | |
| 323 | 5-SCF₃ | | | |
| 324 | 6-SCF₃ | | | |
| 325 | 3-NO₂ | | | |
| 326 | 5-NO₂ | | | |
| 327 | 6-NO₂ | | | |
| 328 | 3-CN | | | |
| 329 | 5-CN | | | |
| 330 | 6-CN | | | |
| 331 | 5,6-[—CH=CH—CH=CH—] | | | |
| 332 | 3,5-Cl₂ | | | |
| 333 | 3,6-Cl₂ | | | |
| 334 | 5,6-Cl₂ | | | |
| 335 | 3,5-(CH₃)₂ | | | |
| 336 | 3,6-(CH₃)₂ | | | |
| 337 | 5,6-(CH₃)₂ | | | |
TABLE 2d
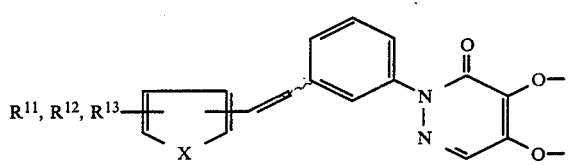
| No. | R¹¹, R¹², R¹³ | X | Linkage | mp (°C.) | cis/trans ratio | H-NMR (ppm) |
|---|---|---|---|---|---|---|
| 338 | H | O | 2 | oil | cis/trans = 1/1 | cis: 7.82 (s; 1H)<br>trans: 7.84 (s; 1H) |
| 339 | H | O | 3 | | | |
| 340 | 3-CH₃ | O | 2 | | | |
| 341 | 4-CH₃ | O | 2 | | | |
| 342 | 5-CH₃ | O | 2 | | | |
| 343 | 2-CH₃ | O | 3 | | | |
| 344 | 4-CH₃ | O | 3 | | | |
| 345 | 5-CH₃ | O | 3 | | | |
| 346 | 3-Cl | O | 2 | | | |
| 247 | 4-Cl | O | 2 | | | |
| 348 | 5-Cl | O | 2 | | | |
| 349 | 3-Br | O | 2 | | | |
| 350 | 4-Br | O | 2 | | | |
| 351 | 5-Br | O | 2 | | | |
| 352 | 2-Cl | O | 3 | | | |
| 353 | 4-Cl | O | 3 | | | |
| 354 | 5-Cl | O | 3 | | | |
| 355 | 2-Br | O | 3 | | | |

TABLE 2d-continued

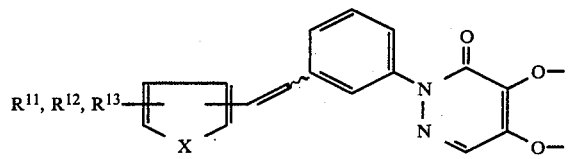

| No. | $R^{11}, R^{12}, R^{13}$ | X | Linkage | mp (°C.) | cis/trans ratio | H-NMR (ppm) |
|---|---|---|---|---|---|---|
| 356 | 4-Br | O | 3 | | | |
| 357 | 5-Br | O | 3 | | | |
| 358 | 3,4-Cl$_2$ | O | 2 | | | |
| 359 | N—CH$_2$ | O | 2 | | | |
| 360 | 4,5-Cl$_2$ | O | 2 | | | |
| 361 | 2,4-Cl$_2$ | O | 3 | | | |
| 362 | 2,5-Cl$_N$—CH$_O$ | 3 | | | | |
| 363 | 4,5-Cl$_2$ | O | 3 | | | |
| 364 | 3,4-Br$_2$ | O | N—CH | | | |
| 365 | 3,5-Br$_2$ | O | 2 | | | |
| 366 | 4,5-Br$_2$ | O | 2 | | | |
| 367 | 2,4-Br$_2$ | O | 3 | | | |
| 368 | 2,5-Br$_2$ | O | 3 | | | |
| 369 | 4,5-Br$_2$ | O | 3 | | | |
| 370 | 3,4,5-Cl$_3$ | O | 2 | | | |
| 371 | 2,4,5-Cl$_3$ | O | 3 | | | |
| 372 | 3,4,5-Br$_3$ | O | 2 | | | |
| 373 | 2,4,5-Br$_3$ | O | 3 | | | |
| 374 | 3-OCH$_3$ | O | 2 | | | |
| 375 | 4-OCH$_3$ | O | 2 | | | |
| 376 | 5-OCH$_3$ | O | 2 | | | |
| 377 | 2-OCH$_3$ | O | 3 | | | |
| 378 | 4-OCH$_3$ | O | 3 | | | |
| 379 | 5-OCH$_3$ | O | 3 | | | |
| 380 | 2,5-(OCH$_3$)$_2$ | O | 3 | | | |
| 381 | 3-OCF$_3$ | O | 2 | | | |
| 382 | 4-OCF$_3$ | O | 2 | | | |
| 383 | 5-OCF$_3$ | O | 2 | | | |
| 384 | 2-OCF$_3$ | O | 3 | | | |
| 385 | 4-OCF$_3$ | O | 3 | | | |
| 386 | 5-OCF$_3$ | O | 3 | | | |
| 387 | 3-SCH$_3$ | O | 2 | | | |
| 388 | 4-SCH$_3$ | O | 2 | | | |
| 389 | 5-SCH$_3$ | O | 2 | | | |
| 390 | 2-SCH$_3$ | O | 3 | | | |
| 391 | 4-SCH$_3$ | O | 3 | | | |
| 392 | 5-SCH$_3$ | O | 3 | | | |
| 393 | 3-SCF$_3$ | O | 2 | | | |
| 394 | 4-SCF$_3$ | O | 2 | | | |
| 395 | 5-SCF$_3$ | O | 2 | | | |
| 396 | 2-SCF$_3$ | O | 3 | | | |
| 397 | 4-SCF$_3$ | O | 3 | | | |
| 398 | 5-SCF$_3$ | O | 3 | | | |
| 399 | 3-NO$_2$ | O | 2 | | | |
| 400 | 4-NO$_2$ | O | 2 | | | |
| 401 | 5-NO$_2$ | O | 2 | | | |
| 402 | 2-NO$_2$ | O | 3 | | | |
| 403 | 4-NO$_2$ | O | 3 | | | |
| 404 | 5-NO$_2$ | O | 3 | | | |
| 405 | 3-CN | O | 2 | | | |
| 406 | 4-CN | O | 2 | | | |
| 407 | 5-CN | O | 2 | | | |
| 408 | 2-CN | O | 3 | | | |
| 409 | 4-CN | O | 3 | | | |
| 410 | 5-CN | O | 3 | | | |
| 411 | 3,4-[—CH=CH—CH=CH—] | O | 2 | | | |
| 412 | 4,5-[—CH=CH—CH=CH—] | O | 2 | | | |
| 413 | 4,5-[—CH=CH—CH=CH—] | O | 3 | | | |
| 414 | H | S | 2 | oil | cis | 7.80 (s; 1H) |
| 415 | H | S | 2 | 101–102 | trans | |
| 416 | H | S | 3 | | | |
| 417 | 3-CH$_3$ | S | 2 | | | |
| 418 | 4-CH$_3$ | S | 2 | | | |
| 419 | 5-CH$_3$ | S | 2 | | | |
| 420 | 2-CH$_3$ | S | 3 | | | |
| 421 | 4-CH$_3$ | S | 3 | | | |
| 422 | 5-CH$_3$ | S | 3 | | | |
| 423 | 3-Cl | S | 2 | | | |
| 424 | 4-Cl | S | 2 | | | |
| 425 | 5-Cl | S | 2 | | | |
| 426 | 3-Br | S | 2 | | | |
| 427 | 4-Br | S | 2 | | | |

TABLE 2d-continued

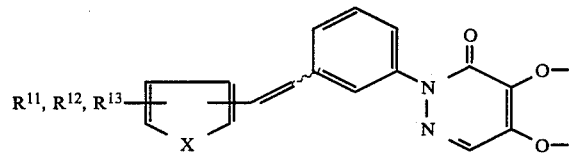

| No. | $R^{11}, R^{12}, R^{13}$ | X | Linkage | mp (°C.) | cis/trans ratio | H-NMR (ppm) |
|---|---|---|---|---|---|---|
| 428 | 5-Br | S | 2 | | | |
| 429 | 2-Cl | S | 3 | | | |
| 430 | 4-Cl | S | 3 | | | |
| 431 | 5-Cl | S | 3 | | | |
| 432 | 2-Br | S | 3 | | | |
| 433 | 4-Br | S | 3 | | | |
| 434 | 5-Br | S | 3 | | | |
| 435 | 3,4-$Cl_2$ | S | 2 | | | |
| 436 | 3,5-$Cl_2$ | S | 2 | | | |
| 437 | 4,5-$Cl_2$ | S | 2 | | | |
| 438 | 2,4-$Cl_2$ | S | 3 | | | |
| 439 | 2,5-$Cl_2$ | S | 3 | | | |
| 440 | 4,5-$Cl_2$ | S | 3 | | | |
| 441 | 3,4-$Br_2$ | S | 2 | | | |
| 442 | 3,5-$Br_2$ | S | 2 | | | |
| 443 | 4,5-$Br_2$ | S | 2 | | | |
| 444 | 2,4-$Br_2$ | S | 3 | | | |
| 445 | 2,5-$Br_2$ | S | 3 | | | |
| 446 | 4,5-$Br_2$ | S | 3 | | | |
| 447 | 3,4,5-$Cl_3$ | S | 2 | | | |
| 448 | 2,4,5-$Cl_3$ | S | 3 | | | |
| 449 | 3,4,5-$Br_3$ | S | 2 | | | |
| 450 | 2,4,5-$Br_3$ | S | 3 | | | |
| 451 | 3-$OCH_3$ | S | 2 | | | |
| 452 | 4-$OCH_3$ | S | 2 | | | |
| 453 | 5-$OCH_3$ | S | 2 | | | |
| 454 | 2-$OCH_3$ | S | 3 | | | |
| 455 | 4-$OCH_3$ | S | 3 | | | |
| 456 | 5-$OCH_3$ | S | 3 | | | |
| 457 | 2,5-$(OCH_3)_2$ | S | 3 | | | |
| 458 | 3-$OCF_3$ | S | 2 | | | |
| 459 | 4-$OCF_3$ | S | 2 | | | |
| 460 | 5-$OCF_3$ | S | 2 | | | |
| 461 | 2-$OCF_3$ | S | 3 | | | |
| 462 | 4-$OCF_3$ | S | 3 | | | |
| 463 | 5-$OCF_3$ | S | 3 | | | |
| 464 | 3-$SCH_3$ | S | 2 | | | |
| 465 | 4-$SCH_3$ | S | 2 | | | |
| 466 | 5-$SCH_3$ | S | 2 | | | |
| 467 | 2-$SCH_3$ | S | 3 | | | |
| 468 | 4-$SCH_3$ | S | 3 | | | |
| 469 | 5-$SCH_3$ | S | 3 | | | |
| 470 | 3-$SCF_3$ | S | 2 | | | |
| 471 | 4-$SCF_3$ | S | 2 | | | |
| 472 | 5-$SCF_3$ | S | 2 | | | |
| 473 | 2-$SCF_3$ | S | 3 | | | |
| 474 | 4-$SCF_3$ | S | 3 | | | |
| 475 | 5-$SCF_3$ | S | 3 | | | |
| 476 | 3-$NO_2$ | S | 2 | | | |
| 477 | 4-$NO_2$ | S | 2 | | | |
| 478 | 5-$NO_2$ | S | 2 | | | |
| 479 | 2-$NO_2$ | S | 3 | | | |
| 480 | 4-$NO_2$ | S | 3 | | | |
| 481 | 5-$NO_2$ | S | 3 | | | |
| 482 | 3-CN | S | 2 | | | |
| 483 | 4-CN | S | 2 | | | |
| 484 | 5-CN | S | 2 | | | |
| 485 | 2-CN | S | 3 | | | |
| 486 | 4-CN | S | 3 | | | |
| 487 | 5-CN | S | 3 | | | |
| 488 | 3,4-[—CH=CH—CH=CH—] | S | 2 | | | |
| 489 | 4,5-[—CH=CH—CH=CH—] | S | 2 | | | |
| 490 | 4,5-[—CH=CH—CH=CH—] | S | 3 | | | |
| 491 | H | N—$CH_3$ | 2 | | | |
| 492 | H | N—$C_2H_5$ | 2 | | | |
| 493 | H | N-n$C_3H_7$ | 2 | | | |
| 494 | H | N-i$C_3H_7$ | 2 | | | |
| 495 | H | N—$CH_2C_6H_5$ | 2 | | | |
| 496 | H | N—$C_6H_5$ | 2 | | | |
| 497 | H | N-4-Cl—$C_6H_5$ | 2 | | | |
| 498 | H | N$CH_3$ | 3 | | | |
| 499 | H | N$C_2H_5$ | 3 | | | |

TABLE 2d-continued

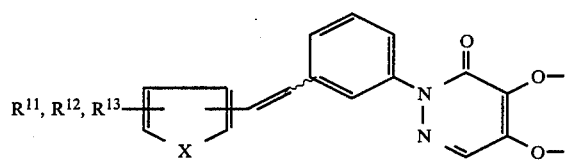

| No. | $R^{11}, R^{12}, R^{13}$ | X | Linkage | mp (°C.) | cis/trans ratio | H-NMR (ppm) |
|---|---|---|---|---|---|---|
| 500 | H | $NnC_3H_7$ | 3 | | | |
| 501 | H | $N\text{-}iC_3H_7$ | 3 | | | |
| 502 | H | $N\text{—}CH_2C_6H_5$ | 3 | | | |
| 503 | H | $N\text{—}C_6H_5$ | 3 | | | |
| 504 | H | $N\text{-4-}ClC_6H_5$ | 3 | | | |
| 505 | 4,5-[—CH=CH—CH=CH—] | $N\text{—}CH_3$ | 2 | | | |
| 506 | 4,5-[—CH=CH—CH=CH—] | $N\text{-}CH_2C_6H_5$ | 2 | | | |
| 507 | 4,5-[—CH=CH—CH=CH—] | $N\text{-}CH_3$ | 3 | | | |
| 508 | 4,5-[—CH=CH—CH=CH—] | $N\text{-}CH_2C_6H_5$ | 3 | | | |

TABLE 2e

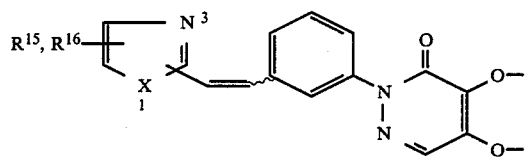

| No. | $R^{15}, R^{16}$ | X | Linkage | mp (°C.) | cis/trans ratio | H-NMR (ppm) |
|---|---|---|---|---|---|---|
| 509 | H | O | 2 | | | |
| 510 | 4-$CH_3$ | O | 2 | | | |
| 511 | 5-$CH_3$ | O | 2 | | | |
| 512 | 2-$CH_3$ | O | 4 | | | |
| 513 | 2-$CH_3$ | O | 5 | | | |
| 514 | 4-$CF_3$ | O | 2 | | | |
| 515 | 5-$CF_3$ | O | 2 | | | |
| 516 | 2-$CF_3$ | O | 4 | | | |
| 517 | 2-$CF_3$ | O | 5 | | | |
| 518 | 2-$OCH_3$ | O | 5 | | | |
| 519 | 2-$SCF_3$ | O | 5 | | | |
| 520 | 2-Cl | O | 5 | | | |
| 521 | 2-$NO_2$ | O | 5 | | | |
| 522 | 2-CN | O | 5 | | | |
| 523 | 4,5-[—CH=CH—CH=CH—] | O | 2 | | | |
| 524 | 4,5-[—($CH_3)_2$—] | O | 2 | | | |
| 525 | H | S | 2 | | | |
| 526 | 4-$CH_3$ | S | 2 | | | |
| 527 | 5-$CH_3$ | S | 2 | | | |
| 528 | 2-$CH_3$ | S | 4 | | | |
| 529 | 2-$CH_3$ | S | 5 | | | |
| 530 | 4-$CF_3$ | S | 2 | | | |
| 531 | 5-$CF_3$ | S | 2 | | | |
| 532 | 2-$CF_3$ | S | 4 | | | |
| 533 | 2-$CF_3$ | S | 5 | | | |
| 534 | 2-$OCF_3$ | S | 5 | | | |
| 535 | 2-$SCF_3$ | S | 5 | | | |
| 536 | 2-Cl | S | 5 | | | |
| 537 | 2-$NO_2$ | S | 5 | | | |
| 538 | 2-CN | S | 5 | | | |
| 539 | 4,5-$(CH_3)_2$ | S | 2 | | | |
| 540 | 4,5-[—CH=CH—CH=CH—] | S | 2 | | | |
| 541 | H | $NCH_3$ | 2 | | | |
| 542 | 4-$CH_3$ | $NCH_3$ | 2 | | | |
| 543 | 5-$CH_3$ | $NCH_3$ | 2 | | | |
| 544 | 2-$CH_3$ | $NCH_3$ | 4 | | | |
| 545 | 2-$CH_3$ | $NCH_3$ | 5 | | | |
| 546 | 4-$CF_3$ | $NCH_3$ | 2 | | | |
| 547 | 5-$CF_3$ | $NCH_3$ | 2 | | | |
| 548 | 2-$CF_3$ | $NCH_3$ | 4 | | | |
| 549 | 2-$CF_3$ | $NCH_3$ | 5 | | | |
| 550 | 2-$OCF_3$ | $NCH_3$ | 4 | | | |
| 551 | 2-$SCF_3$ | $NCH_3$ | 4 | | | |
| 552 | 2-$OCH_3$ | $NCH_3$ | 4 | | | |
| 553 | 2-$SCH_3$ | $NCH_3$ | 4 | | | |
| 554 | 2-Cl | $NCH_3$ | 4 | | | |
| 555 | 2-$NO_2$ | $NCH_3$ | 4 | | | |
| 556 | 2-CN | $NCH_3$ | 4 | | | |
| 557 | 4,5-[—($CH_3)_2$—] | $NCH_3$ | 2 | | | |

TABLE 2e-continued

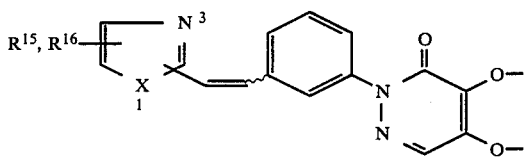

| No. | $R^{15}, R^{16}$ | X | Linkage | mp (°C.) | cis/trans ratio | H-NMR (ppm) |
|---|---|---|---|---|---|---|
| 558 | 4,5-[—CH=CH—CH=CH—] | $NCH_3$ | 2 | | | |

TABLE 2f

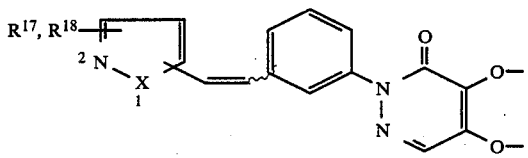

| No. | $R^{17}, R^{18}$ | X | Linkage | mp (°C.) | cis/trans ratio | H-NMR (ppm) |
|---|---|---|---|---|---|---|
| 559 | H | O | 5 | | | |
| 560 | 3-$CH_3$ | O | 5 | | | |
| 561 | 3-$C_2H_5$ | O | 5 | 50–54 | cis | |
| 562 | 3-$nC_3H_7$ | O | 5 | | | |
| 563 | 3-$iC_3H_7$ | O | 5 | oil | cis/trans = 2/1 | cis: 7.81 (s; 1H) trans: 7.86 (s; 1H) |
| 564 | 3-$nC_4H_9$ | O | 5 | | | |
| 565 | 3-$iC_4H_9$ | O | 5 | oil | cis | 7.82 (s; 1H) |
| 566 | 3-sec$C_4H_9$ | O | 5 | | | |
| 567 | 3-t$C_4H_9$ | O | 5 | | | |
| 568 | 3-n-$C_5H_{11}$ | O | 5 | | | |
| 569 | 3-n-$C_6H_{13}$ | O | 5 | | | |
| 570 | 3-$C_6H_5$ | O | 5 | | | |
| 571 | 3-4′Cl—$C_6H_4$ | O | 5 | | | |
| 572 | 3-4′$CH_3$—$C_6H_4$ | O | 5 | | | |
| 573 | 3-4′$CF_3$—$C_6H_4$ | O | 5 | | | |
| 574 | 3-$CH_3OCH_2$ | O | 5 | | | |
| 575 | 3-2′furyl | O | 5 | | | |
| 576 | 3-3′furyl | O | 5 | | | |
| 577 | 3-2′thienyl | O | 5 | | | |
| 578 | 3-3′thienyl | O | 5 | | | |
| 579 | 3-(2′-tetrahydropyranyl) | O | 5 | | | |
| 580 | 3-(3′-tetrahydropyranyl) | O | 5 | | | |
| 581 | 3-(4′-tetrahydropyranyl) | O | 5 | | | |
| 582 | 3-(2′-tetrahydrothiopyranyl) | O | 5 | | | |
| 583 | 3-(3′-tetrahydrothiopyranyl) | O | 5 | | | |
| 584 | 3-(4′-tetrahydrothiopyranyl) | O | 5 | | | |
| 585 | 3-cyclo-$C_3H_5$ | O | 5 | | | |
| 586 | 3-cyclo-$C_4H_7$ | O | 5 | | | |
| 587 | 3-cyclo-$C_5H_9$ | O | 5 | | | |
| 588 | 3-cyclo-$C_6H_{11}$ | O | 5 | | | |
| 589 | 3-cyclo-$C_7H_{13}$ | O | 5 | | | |
| 590 | 3,5($CH_3)_2$ | O | 4 | | | |
| 591 | 3-$CH_3$ | S | 5 | | | |
| 592 | 3-$C_2H_5$ | S | 5 | | | |
| 593 | 3-$nC_3H_7$ | S | 5 | | | |
| 594 | 3-$iC_3H_7$ | S | 5 | | | |
| 595 | H | $NCH_3$ | 4 | oil | cis/trans = 1/2 | cis: 7.80 (s; 1H); trans: 7.83 (s; 1H) |
| 596 | H | N—$C_4H_9$ | 4 | | | |
| 597 | 3-$CH_3$ | $NCH_3$ | 4 | | | |
| 598 | 3-$CH_3$ | $NCH_3$ | 5 | | | |
| 599 | 5-$CH_3$ | $NCH_3$ | 4 | | | |

TABLE 2g

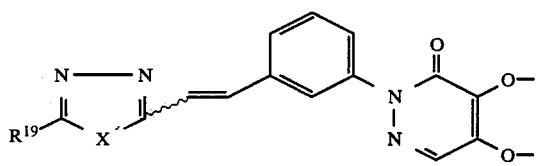

| No. | $R^{19}$ | X | mp (°C.) | cis/trans ratio | H-NMR (ppm) |
|---|---|---|---|---|---|
| 600 | H | O | | | |
| 601 | $CH_3$ | O | | | |
| 602 | $C_2H_5$ | O | | | |
| 603 | $nC_3H_7$ | O | | | |
| 604 | $n\text{-}C_4H_9$ | O | | | |
| 605 | $t\text{-}C_4H_9$ | O | | | |
| 606 | $CF_3$ | O | | | |
| 607 | $OCH_3$ | O | | | |
| 608 | $OCF_3$ | O | | | |
| 609 | $SCH_3$ | O | | | |
| 610 | $SCF_3$ | O | | | |

TABLE 2g-continued

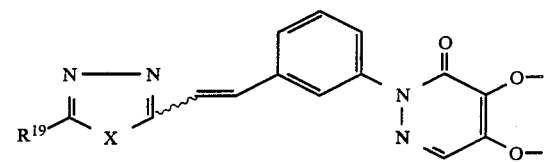

| No. | $R^{19}$ | X | mp (°C.) | cis/trans ratio | H-NMR (ppm) |
|---|---|---|---|---|---|
| 611 | H | S | | | |
| 612 | $CH_3$ | S | | | |
| 613 | $C_2H_5$ | S | | | |
| 614 | $n\text{-}C_3H_7$ | S | | | |
| 615 | $n\text{-}C_4H_9$ | S | | | |
| 616 | $t\text{-}C_4H_9$ | S | | | |
| 617 | $CF_3$ | S | | | |
| 618 | $OCH_3$ | S | | | |
| 619 | $OCF_3$ | S | | | |
| 620 | $SCH_3$ | S | | | |
| 621 | $SCF_3$ | S | | | |

TABLE 2h

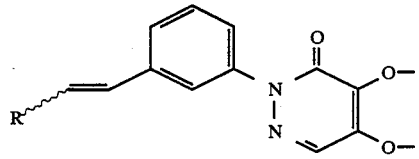

| No. | R | mp (°C.) | cis/trans ratio | H-NMR (ppm) |
|---|---|---|---|---|
| 622 | Me | | | |
| 623 | Et | oil | cis/trans = 1/1 | cis: 7.81 (s; 1 H), trans: 7.82 (s; 1 H) |
| 624 | $n\text{-}C_3H_7$ | | | |
| 625 | $i\text{-}C_3H_7$ | | | |
| 626 | $n\text{-}C_4H_9$ | oil | cis/trans = 1/1 | cis: 7.80 (s; 1 H); trans: 7.81 (s; 1 H) |
| 627 | $i\text{-}C_4H_9$ | | | |
| 628 | $sec\text{-}C_4H_9$ | | | |
| 629 | $t\text{-}C_4H_9$ | | | |
| 630 | $n\text{-}C_5H_{11}$ | | | |
| 631 | $n\text{-}C_6H_{13}$ | | | |
| 632 | $n\text{-}C_7H_{15}$ | | | |
| 633 | $n\text{-}C_8H_{17}$ | | | |
| 634 | $cyclo\text{-}C_3H_5$ | oil | cis/trans = 1/1 | cis: 7.81 (s; 1 H); trans: 7.82 (s; 1 H) |
| 635 | $cyclo\text{-}C_4H_7$ | | | |
| 636 | $cyclo\text{-}C_5H_9$ | | | |
| 637 | $cyclo\text{-}C_6H_{11}$ | | | |
| 638 | $cyclo\text{-}C_7H_{13}$ | | | |
| 639 | $cyclo\text{-}C_8H_{15}$ | | | |
| 640 | 2-norbornyl | | | |
| 641 | 2-tetrahydrofuryl | | | |
| 642 | 3-tetrahydrofuryl | | | |
| 643 | 2-tetrahydropyranyl | | | |
| 644 | 3-tetrahydropyranyl | | | |
| 645 | 4-tetrahydropyranyl | | | |
| 646 | 2-tetrahydrothienyl | | | |
| 647 | 3-tetrahydrothienyl | | | |
| 648 | 2-tetrahydrothiopyranyl | | | |
| 649 | 3-tetrahydrothiopyranyl | | | |
| 650 | 4-tetrahydrothiopyranyl | | | |
| 651 | 2-dioxanyl-(1,4)- | | | |
| 652 | benzyl | | | |
| 653 | 2-F-benzyl | oil | cis/trans = 1/9 | cis: 7.79 (s; 1 H); trans: 7.81 (s; 1 H) |
| 654 | 3-F-benzyl | | | |
| 655 | 4-F-benzyl | | | |
| 656 | 2-Cl-benzyl | | | |
| 657 | 3-Cl-benzyl | | | |
| 658 | 4-Cl-benzyl | | | |
| 659 | $2\text{-}CH_3\text{-}benzyl$ | | | |
| 660 | $3\text{-}CH_3\text{-}benzyl$ | | | |
| 661 | $4\text{-}CH_3\text{-}benzyl$ | | | |
| 662 | $2\text{-}CF_3\text{-}benzyl$ | | | |
| 663 | $3\text{-}CF_3\text{-}benzyl$ | | | |

TABLE 2h-continued

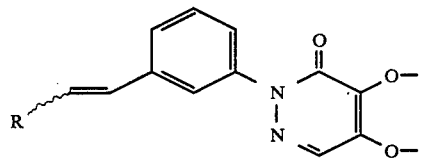

| No. | R | mp (°C.) | cis/trans ratio | H-NMR (ppm) |
|---|---|---|---|---|
| 664 | 4-CF$_3$-benzyl | | | |
| 665 | 2-OCH$_3$-benzyl | | | |
| 666 | 3-OCH$_3$-benzyl | | | |
| 667 | 4-OCH$_3$-benzyl | | | |
| 668 | 2-OCF$_3$-benzyl | | | |
| 669 | 3-OCF$_3$-benzyl | | | |
| 670 | 4-OCF$_3$-benzyl | | | |
| 671 | 2-SCH$_3$-benzyl | | | |
| 672 | 3-SCH$_3$-benzyl | | | |
| 673 | 4-SCH$_3$-benzyl | | | |
| 674 | 2-SCF$_3$-benzyl | | | |
| 675 | 3-SCF$_3$-benzyl | | | |
| 676 | 4-SCF$_3$-benzyl | | | |
| 677 | 2-CN-benzyl | | | |
| 678 | 3-CN-benzyl | | | |
| 679 | 4-CN-benzyl | | | |
| 680 | styryl | 134–140 | trans-trans | |
| 681 | styryl | 83–86 | trans-cis | |
| 682 | 2-F-styryl | | | |
| 683 | 3-F-styryl | | | |
| 684 | 4-F-styryl | | | |
| 685 | 2-Cl-styryl | | | |
| 686 | 3-Cl-styryl | | | |
| 687 | 4-Cl-styryl | | | |
| 688 | 2-CH$_3$-styryl | | | |
| 689 | 3-CH$_3$-styryl | | | |
| 690 | 4-CH$_3$-styryl | | | |
| 691 | 2-CF$_3$-styryl | | | |
| 692 | 3-CF$_3$-styryl | | | |
| 693 | 4-CF$_3$-styryl | | | |
| 694 | 2-OCH$_3$-styryl | | | |
| 695 | 3-OCH$_3$-styryl | | | |
| 696 | 4-OCH$_3$-styryl | | | |
| 697 | 2-OCF$_3$-styryl | | | |
| 698 | 3-OCF$_3$-styryl | | | |
| 699 | 4-OCF$_3$-styryl | | | |
| 700 | 2-SCH$_3$-styryl | | | |
| 701 | 3-SCH$_3$-styryl | | | |
| 702 | 4-SCH$_3$-styryl | | | |
| 703 | 2-SCF$_3$-styryl | | | |
| 704 | 3-SCF$_3$-styryl | | | |
| 705 | 4-SCF$_3$-styryl | | | |
| 706 | 2-CN-styryl | | | |
| 707 | 3-CN-styryl | | | |
| 708 | 4-CN-styryl | | | |
| 709 | 2-NO$_2$-styryl | | | |
| 710 | 3-NO$_2$-styryl | | | |
| 711 | 4-NO$_2$-styryl | | | |

USE EXAMPLES

The herbicidal action on plant growth is demonstrated by the following greenhouse experiments:

The vessels employed were plastic flowerpots having a volume of 300 cm$^3$ and filled with a sandy loam containing about 3.0% humus. The seeds of the test plants were sown separately, according to species.

For the postemergence treatment, either plants which had been sown in the pots and grown there were selected, or they were cultivated separately as seedlings and transplanted to the pots a few days before being treated.

Depending on growth form, the plants were grown to a height of from 3 to 15 cm before being treated with the active ingredients which were suspended or emulsified in water and sprayed through finely distributing nozzles. The application rate for postemergence treatment was 0.06 kg of active ingredient per hectare.

The pots were set up in the greenhouse, species from warmer climates in warmer areas (20° to 35° C.) and species from moderate climates at 10° to 20° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the greenhouse experiments were:

| Abbreviation | Latin name | Common name |
|---|---|---|
| AMARE | *Amaranthus retroflexus* | redroot pigweed |

| Abbreviation | Latin name | Common name |
| --- | --- | --- |
| CASTO | *Cassia tora* | sicklepod |
| CHEAL | *Chenopodium album* | lambsquarters |
| GOSHI | *Gossypium hirsutum* | cotton |
| HELAN | *Helianthus annus* | sunflowers |

The following active ingredients described in DE-A-3 617 997 were used for comparison purposes:

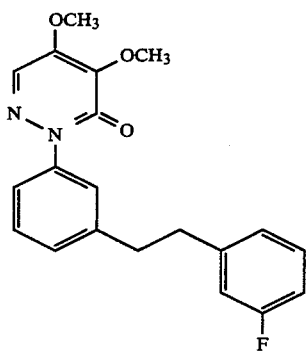

A (compound no. 30 in DE-A 3 617 997)

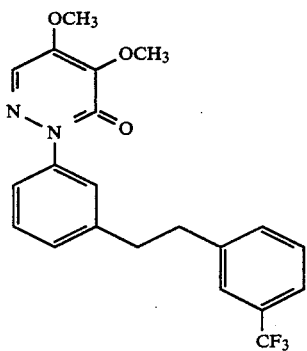

B (compound no. 27 in DE-A 3 617 997)

Compounds nos. 43 and 39, applied postemergence at a rate of 0.06 kg/ha, combated unwanted broadleaved plants excellently, and were tolerated much better by cotton and sunflowers than the prior art active ingredients A and B.

We claim:

1. 2-Phenylpyridazin-3-one compounds of the formulae

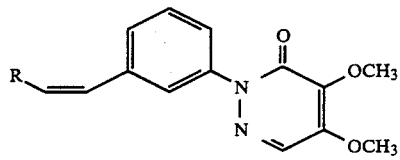

Ia

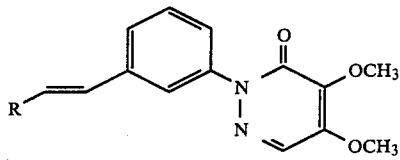

Ib where R is $C_1$-$C_8$-alkyl; benzyl, where the aromatic ring may carry 1 to 3 of the substituents fluorine, chlorine, bromine, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio or cyano; $C_3$-$C_8$-cycloalkyl which may carry 1 to 3 of the substituents $C_1$-$C_4$-alkyl, $C_1$-$C_4$-haloalkyl, $C_1$-$C_4$-alkoxy or $C_1$-$C_4$-haloalkoxy; styryl, where the aromatic ring may carry 1 to 3 of the substituents nitro, fluorine, chlorine, bromine, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio or cyano; a 6-membered aromatic ring which may be benzo-fused and may carry 1 to 4 of the substituents $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, fluorine, chlorine, bromine, nitro, cyano, amino, di-$C_1$-$C_4$-alkylamino, $C_2$-$C_6$-acylamino, $C_1$-$C_4$-alkoxycarbonyl, phenoxy or phenylthio.

2. A compound as set forth in claim 1, where R is substituted phenyl of the structure

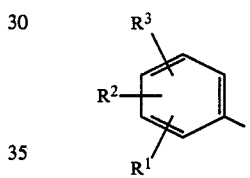

where $R^1$, $R^2$ and $R^3$ are identical or different and each denotes hydrogen, $C_1$-$C_6$-alkyl, $C_1$-$C_6$-haloalkyl, $C_1$-$C_7$-alkoxy, $C_1$-$C_6$-haloalkoxy, $C_1$-$C_6$-alkylthio, $C_1$-$C_6$-haloalkylthio, phenyl, substituted or unsubstituted aryloxy, substituted or unsubstituted arylthio, fluorine, chlorine, bromine, nitro, amino, dialkylamino, acylamino, diacylamino, cyano or a carboxylate, or R, together with the phenyl nucleus, denotes naphthyl.

3. A herbicidal composition which comprises an inert additive and a herbicidally effective amount of a 2-phenylpyridazin-3-one compound of the formulae Ia and/or Ib as set forth in claim 1.

4. A process for combating unwanted plant growth, wherein the unwanted plants and/or their habitat are treated with a herbicidally effective amount of a 2-phenylpyridazin-3-one compound Ia and/or Ib as set forth in claim 1.

5. A compound as set forth in claim 2, wherein $R^1$ is 3-$CF_3$ and $R^2$ and $R^3$ are hydrogen.

6. A compound as set forth in claim 2, wherein $R^1$ is 3-F and $R^2$ and $R^3$ are hydrogen.

7. A process for combatting unwanted plant growth which comprises applying to the unwanted plants of their habitat a herbicidally effective amount of a compound as set forth in claim 2.

8. A process for combatting unwanted plant growth which comprises applying to the unwanted plants or their habitat a herbicidally effective amount of a compound as set forth in claim 5.

9. A process for combatting unwanted plant growth which comprises applying to the unwanted plants or their habitat a herbicidally effective amount of a compound as set forth in claim 6.

* * * * *

UNITED STATES PATENT AND TRADEMARK OFFICE
CERTIFICATE OF CORRECTION

PATENT NO. : 4,941,911

DATED : July 17, 1990

INVENTOR(S) : Wolfgang FREUND et al.

It is certified that error appears in the above-identified patent and that said Letters Patent is hereby corrected as shown below:

ON THE COVER PAGE insert --Foreign Application Priority Data

March 10, 1988   DE   Federal Republic of Germany ... 3807896--

Claim 2, Line 6
Column 34, line 38
"$C_{1'-c6}$-haloalkoxy" should read --$C_{1-6}$-haloalkoxy--."

Claim 7, Line 2
Column 34, line 58
"of" should read --or--

Signed and Sealed this

Third Day of December, 1991

Attest:

HARRY F. MANBECK, JR.

*Attesting Officer*  *Commissioner of Patents and Trademarks*